(12) United States Patent
Davis, Jr.

(10) Patent No.: US 8,753,567 B1
(45) Date of Patent: Jun. 17, 2014

(54) METHOD AND KIT FOR CONTROLLING ODOR IN AN AIR SCRUBBER

(75) Inventor: Charley John Davis, Jr., Crab Orchard, KY (US)

(73) Assignee: Hydro-Solutions, Inc., Louisville, KY (US)

( * ) Notice: Subject to any disclaimer, the term of this patent is extended or adjusted under 35 U.S.C. 154(b) by 430 days.

(21) Appl. No.: 13/023,658

(22) Filed: Feb. 9, 2011

Related U.S. Application Data

(60) Provisional application No. 61/328,741, filed on Apr. 28, 2010.

(51) Int. Cl.
*A61L 9/00* (2006.01)

(52) U.S. Cl.
USPC .................................. 422/5; 422/4

(58) Field of Classification Search
USPC ......................... 422/5, 120, 123, 4
See application file for complete search history.

(56) References Cited

U.S. PATENT DOCUMENTS

| | | | |
|---|---|---|---|
| 4,007,262 A * | 2/1977 | Bowers | 424/76.7 |
| 4,070,300 A * | 1/1978 | Moroni et al. | 252/190 |
| 4,902,489 A | 2/1990 | Watanabe | |
| 4,919,925 A * | 4/1990 | Ueda et al. | 424/76.1 |
| 5,054,434 A | 10/1991 | Wax et al. | |
| 5,223,230 A | 6/1993 | Takemura et al. | |
| 5,433,864 A | 7/1995 | Yun et al. | |
| 5,635,069 A | 6/1997 | Boss et al. | |
| 5,849,984 A | 12/1998 | Kim et al. | |
| 5,866,112 A | 2/1999 | Jones et al. | |
| 6,013,196 A * | 1/2000 | Morlec et al. | 252/192 |
| 6,083,386 A | 7/2000 | Lloyd | |
| 6,413,506 B1 | 7/2002 | Levi et al. | |
| 7,000,333 B2 | 2/2006 | Yarem | |
| 2005/0255078 A1 * | 11/2005 | Sakamoto et al. | 424/76.1 |
| 2008/0193588 A1 | 8/2008 | Yamamoto | |
| 2009/0130764 A1 | 5/2009 | Stanforth | |

* cited by examiner

*Primary Examiner* — Regina M Yoo
(74) *Attorney, Agent, or Firm* — Stites & Harbison PLLC; Mandy Wilson Decker

(57) ABSTRACT

A method for controlling odor in an air scrubber makes use of a dicarboxylic acid, which is placed in contact with odor-causing contaminants, and which is maintained at a pH of about 5.0 to about 8.0.

12 Claims, 3 Drawing Sheets

US 8,753,567 B1

METHOD AND KIT FOR CONTROLLING ODOR IN AN AIR SCRUBBER

RELATED APPLICATIONS

This application claims priority from U.S. Provisional Application Ser. No. 61/328,741 filed Apr. 28, 2010, the entire disclosure of which is incorporated herein by this reference.

TECHNICAL FIELD

The presently-disclosed subject matter relates to controlling odor in an air scrubber, for example, an air scrubber used in a plant such as an animal product rendering plant.

INTRODUCTION

Air scrubbers are devices used to control emission of pollutants into the air, for example, emission of odorous gasses. Various materials can be added to water used in air scrubbers to assist with the removal or control of such emissions. Such materials can include oxidizing additives, such as, sodium hypochlorite, sodium chlorite, sodium chlorate, chlorine gas, chlorine dioxide gas, peroxyacetic acid, potassium sermanganate, and bromine; or non-oxidizing additives, such as, perfume mixtures and mineral acids. Such additives can further include organic acids, such as acetic acid, ketones, aldehydes, oils, and surfactants.

Known materials and related methods for use in air scrubbers to assist with the removal or control of undesirable emissions have certain drawbacks. For example, when air streams on air treatment devices using such known materials and method are tested, relatively low rates of removal of the emission are found.

Furthermore, such known materials and methods are limiting in that they are not conducive to use with most scale inhibitors and/or oil dispersants, and are additionally incompatible with water soluble or solubilized ketones and aldehydes, producing organic acids that may actually contribute to undesirable emissions.

Additionally, those known materials and methods that make use of oxidizing additives can destroy or diminish the effectiveness of organic scale inhibitors and/or oil dispersants. Many of the known materials will also undesirably react with water-soluble or solubilized ketones and aldehydes.

Accordingly, there remains a need in the art for a method and kit for controlling odor in an air scrubber, which satisfactorily addresses above-identified drawbacks and/or other drawbacks of known materials and methods.

DESCRIPTION OF EXEMPLARY EMBODIMENTS

Figure 1:
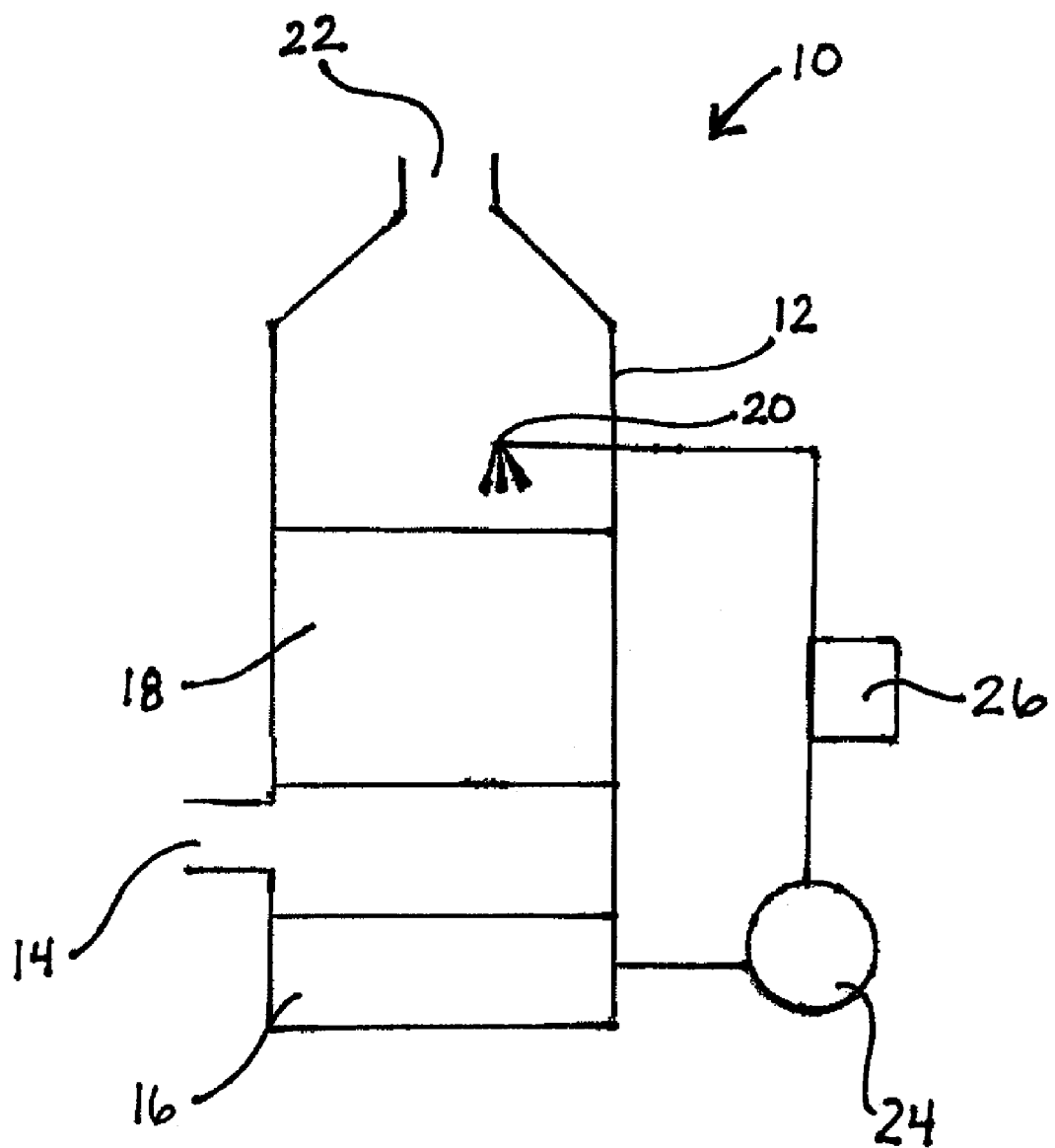
FIG. 1 is a schematic representation of a media-filled air scrubber that can be used in accordance with embodiments of the presently-disclosed subject matter.

The presently-disclosed subject matter includes methods and kits for controlling odor in an air scrubber.

As used herein, the term "air scrubber" refers to any equipment, including industrial equipment, that makes use of a solution for controlling contaminants in the air of a particular environment, including, but not limited to, media-filled air scrubbers, e.g., packed, plate, bubble, etc., spray-type air scrubbers or spray tower air scrubbers, cross-flow air scrubbers, Venturi scrubbers, knock down chambers, and the like. The solution for controlling contaminants can be aqueous, i.e., water-based. The air scrubber can re-use and/or re-circulate the solution that comes in contact with contaminants from the air. Specific examples of air scrubbers that can be used with the presently-disclosed subject matter include, but are not limited to, air scrubbers manufactured by SCP Control Inc. (Minneapolis, Minn.), Millpoint (Greensboro, N.C.), IES (Mounds View, Minn.), and AC Corporation (Greensboro, N.C.).

As used herein, the term "contaminant" refers to particles or molecules in the air of a particular environment that are desired to be removed or reduced in quantity and/or concentration. Examples of such contaminants, include, but are not limited to, odor-causing contaminants, such as primary amines, secondary amines, tertiary amines, ammonia, mercaptans, thiols, hydrogen sulfide, other sulfide compounds, and/or combinations thereof. In some embodiments, for example when the environment is an animal processing or rendering facility, contaminants can include oil contaminants. The type of oil rendered or cooked at a facility can correlate to a type of oil contaminant found in the air scrubber; for example, in facilities processing chickens, grease or oil found in the air scrubber can be chicken grease or oil, and in facilities processing several types of raw materials, grease or oil found in the air scrubber can be derived for the various raw materials. Oil contaminants can include, for example, condensed or captured chicken fat, beef tallow, or pork lard.

The term "controlling", when herein used to refer to control of a contaminant, such as an odor-causing contaminant, refers to a removal or a reduction in quantity and/or concentration of contaminants, such as odor-causing particles or molecules, in the air of a particular environment. An environment can be, for example, a container, a room, a factory, a processing plant (e.g., meat, poultry, and/or fish processing and/or by products facility), food industries facility, etc.

In some embodiments, the presently-disclosed subject matter includes a method for controlling odor in an air scrubber including: providing a dicarboxylic acid, contacting the dicarboxylic acid with an odor-causing contaminant; and maintaining the dicarboxylic acid in a solution at a desired pH.

When the dicarboxylic acid is contacted with an odor-causing contaminant, it beneficially reacts with that contaminant to remove it from the air. As such, air that contains contaminants will flow into the air scrubber, where the dicarboxylic acid is placed in contact with the contaminant and reacts with the contaminant to remove it from the air, such that air flowing out of the air scrubber has a reduced quantity and/or concentration of contaminants as compared to air flowing into the air scrubber.

In some embodiments of the method, contacting the dicarboxylic acid with an odor-causing contaminant includes feeding the dicarboxylic acid into water circulating in the air scrubber. In this regard, it can be desirable to control the concentration of the dicarboxylic acid in the circulating water. In some embodiments, it can be desirable to provide and/or maintain the dicarboxylic acid at a concentration of at least about 100 part per million. In some embodiments, it can be desirable to provide and/or maintain the dicarboxylic acid at a concentration of about 100 parts per million to about 2000 parts per million. In some embodiments, it can be desirable to provide and/or maintain the dicarboxylic acid at a concentration of about 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 parts per million. In some embodiments, it can be desirable to continuously or periodically adjust the concentration of dicarboxylic acid to at least about a stoichiometric level to match the odor-causing contaminants, or to exceed the stoichiometric level matching the odor-causing contaminants.

When the circulating dicarboxylic acid solution reacts with contaminants, removing them from the air, the dicarboxylic acid solution can be said to approach and reach saturation. As such, embodiments of the presently-disclosed subject matter include controlling the saturation of the solution circulating in the air scrubber. In this manner, dicarboxylic acid in the circulating water can remain available for reaction with contaminants in the air, to continuously facilitate their removal from the air. For example, the concentration of the dicarboxylic acid that has reacted with contaminants can be controlled through the use of bleed or blow down of the circulating water into a sewer, where it can be treated at a waste treatment facility.

As will understood by those of ordinary skill in the art upon study of this application, controlling the concentration of dicarboxylic acid can allow for control over the quantity and/or concentration of contaminants in the air flowing out of the air scrubber. In this regard, in some embodiments, the concentration of dicarboxylic acid can be provided and/or maintained with a goal of minimizing the concentration of contaminants in the air flowing out of the air scrubber.

In some embodiments, the concentration of dicarboxylic acid can be provided and/or maintained with a goal of providing for a particular target emission concentration, or range of concentrations, of contaminants in the air flowing out of the air scrubber.

As noted above, in some embodiments of the presently-disclosed method the dicarboxylic acid solution is maintained at a desired pH. The present inventors have discovered that maintaining the pH within certain desired ranges can be beneficial to the efficacy of the method. For example, in some embodiments, the desired pH is between about 5.0 and about 8.0. In some embodiments, the desired pH is about 5.0, about 5.5, about 6.0, about 6.5, about 7.0, about 7.5, or about 8.0. In some embodiments, assessing and maintaining the pH of the circulating solution can be efficiently conducted at such time as the concentration of the dicarboxylic acid is assessed and/or maintained in accordance with the description herein.

As noted herein, the presently-disclosed subject matter includes kits for controlling odor in an air scrubber. In some embodiments, the kit includes a dicarboxylic acid; and instructions for contacting the dicarboxylic acid with an odor-causing contaminant. For example, the kit can include instructions for practicing the method of the presently-disclosed subject matter as described herein.

The dicarboxylic acid that is provided for use in accordance with the presently-disclosed subject matter can be any dicarboxylic acid. For example, in some embodiments, the dicarboxylic acid has the formula:

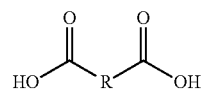

wherein, R is selected from covalent bond, lower alkyl, alkyl, alkenyl, aryl, or any substituted or unsubstituted carbon chain, wherein the resulting dicarboxylic acid is water-soluble. In some embodiments, the dicarboxylic acid can be oxalic acid, malonic acid, succinic acid, glutaric acid, hexanedioic acid, heptanedioic acid, oxtanedioic acid, nonanedioic acid, decanedioic acid, malic acid, phthalic acid, isophthalic acid, terephthalic acid, or combinations thereof. In some embodiments, the dicarboxylic acid is selected from: oxalic acid, malonic acid, succinic acid, glutaric acid, and malic acid. In some embodiments, the dicarboxylic acid is malic acid.

It is noted that exemplary dicarboxylic acids are described herein using chemical structures and/or common names, as will be recognized by those skilled in the art. Such dicarboxylic acids can be identified by alternate nomenclature, e.g., IUPAC, as will be readily known to those skilled in the art, and all such compounds are expressly contemplated as being equivalent to those compounds identified by chemical structure and/or by common name in the present application. For example, as will be understood by those skilled in the art, the term "malic acid" as used herein encompasses at least hydroxybutanedioic acid, L-malic acid, D-malic acid, (−)-malic acid, (+)-malic acid, (S)-hydroxybutanedioic acid, and (R)-hydroxybutanedioic acid. For another example, as will be understood by those skilled in the art, the term "succinic acid" as used herein encompasses at least butanedioic acid and ethane-1,2-dicarboxylic acid. For another example, as will be understood by those skilled in the art, the term "glutaric acid" as used herein encompasses at least pentanedioic acid, propane-1,3-dicarboxylic acid, 1,3-propanedicarboxylic acid, pentanedioic acid, and n-pyrotartaric acid. For another example, as will be understood by those skilled in the art, the term "malonic acid" as used herein encompasses at least propanedioic acid and methanedicarboxylic acid. For another example, as will be understood by those skilled in the art, the term "oxalic acid" as used herein encompasses at least ethanedioic acid.

In some embodiments of the presently-disclosed subject matter, in addition to providing a dicarboxylic acid for feeding into water circulating in the air scrubber, additional components can be provided to improve absorption conditions in the air scrubber. Examples of such additional components include, but are not limited to, scale inhibitors, oil dispersants, surfactants, water-soluble ketones, water-soluble aldehydes, ketones solubilized with surfactants, and aldehydes solubilized with surfactants.

As such, in some embodiments, the presently-disclosed method includes providing a scale inhibitor, an oil dispersant, a surfactant, a water-soluble ketone, a water-soluble aldehyde, or combinations thereof. In some embodiments, the presently-disclosed kit includes a scale inhibitor, an oil dispersant, a surfactant, a water-soluble ketone, a water-soluble aldehyde, or combinations thereof.

In some embodiments, one or more additional components can be mixed with the dicarboxylic acid prior to feeding the mixture into the circulating water. In some embodiments, one or more additional components can be fed into the circulating water simultaneously with the dicarboxylic acid; and/or one or more additional components can be fed into the circulating water prior to and/or after the dicarboxylic acid is fed into the circulating water.

As will be understood by those skilled in the art upon study of the present application, it can be desirable to make use of scale inhibitors, oil dispersants, and/or surfactants when the air scrubber is being operated for an extended period of time, for example, in order to maintain the integrity of the equipment.

As will be understood by those skilled in the art upon study of the present application, the circulating water in the air scrubber can contain different types and amounts of inorganic compounds, and the types and concentrations of inorganic compounds found in the circulating water can be useful in determining whether and how much scale inhibitor can be used to affect desirable efficacy.

As will be understood by those skilled in the art upon study of the present application, the amount and type of oil contaminant(s) found in the airstream can be useful in determining whether, which, and how much oil dispersants and/or surfactants can be used to affect desirable efficacy.

The presently-disclosed subject matter is further illustrated by the following specific but non-limiting examples. The following examples may include compilations of data and/or information that are representative of data and/or information gathered at various times during the course of development and experimentation related to the presently-disclosed subject matter

EXAMPLES

Example 1

FIG. 1 is a diagram of an exemplary packed bed scrubber 10. Packed bed scrubbers are generally constructed of a vertical tank 12 from about two feet in diameter up to about twenty feet in diameter where the influent air enters the scrubber through a duct 14 located above a sump water level 16. The duct 14 is sized to carry a volume of air moved by a fan. The air then travels up through a grating, which supports media (toilerettes, paw rings, etc.) of the scrubber, and on through the media 18. The media is located from about one to about twenty feet above the duct 14. Above the media is located a nozzle configuration 20 comprised of from about one to about fifty nozzles. The nozzles are elevated above the media and configured in such a way to optimize water coverage of the top layer of the media. The air then normally-travels through a de-mister section where droplets of water or mist are captured, falling back to the media. The treated air then exits the scrubber through the effluent stack 22.

Water from the sump 16 is pumped (e.g., using a recirculating pump 24) up through the nozzle configuration on to the media 18 where it travels down through the media 18, returning to the sump 16. As the water travels through the media 18 it spreads out over the media 18 maximizing surface area and intimate air-water contact.

The dicarboxylic acid solution is fed into the sump water 16 or into a suction side of a recirculation pump 24, or into a pressure side of the recirculation pump 24. Normally the solution would be metered in with one of the following: a chemical metering pump, educator, gear pump, progressive cavity pump, or any other pump or device designed to deliver liquid in the required volume. pH control of the sump water is controlled via a pH controller 26 which activates a chemical pump or other device that provides for the addition of an acid or caustic to the sump.

Example 2

Figure 2:
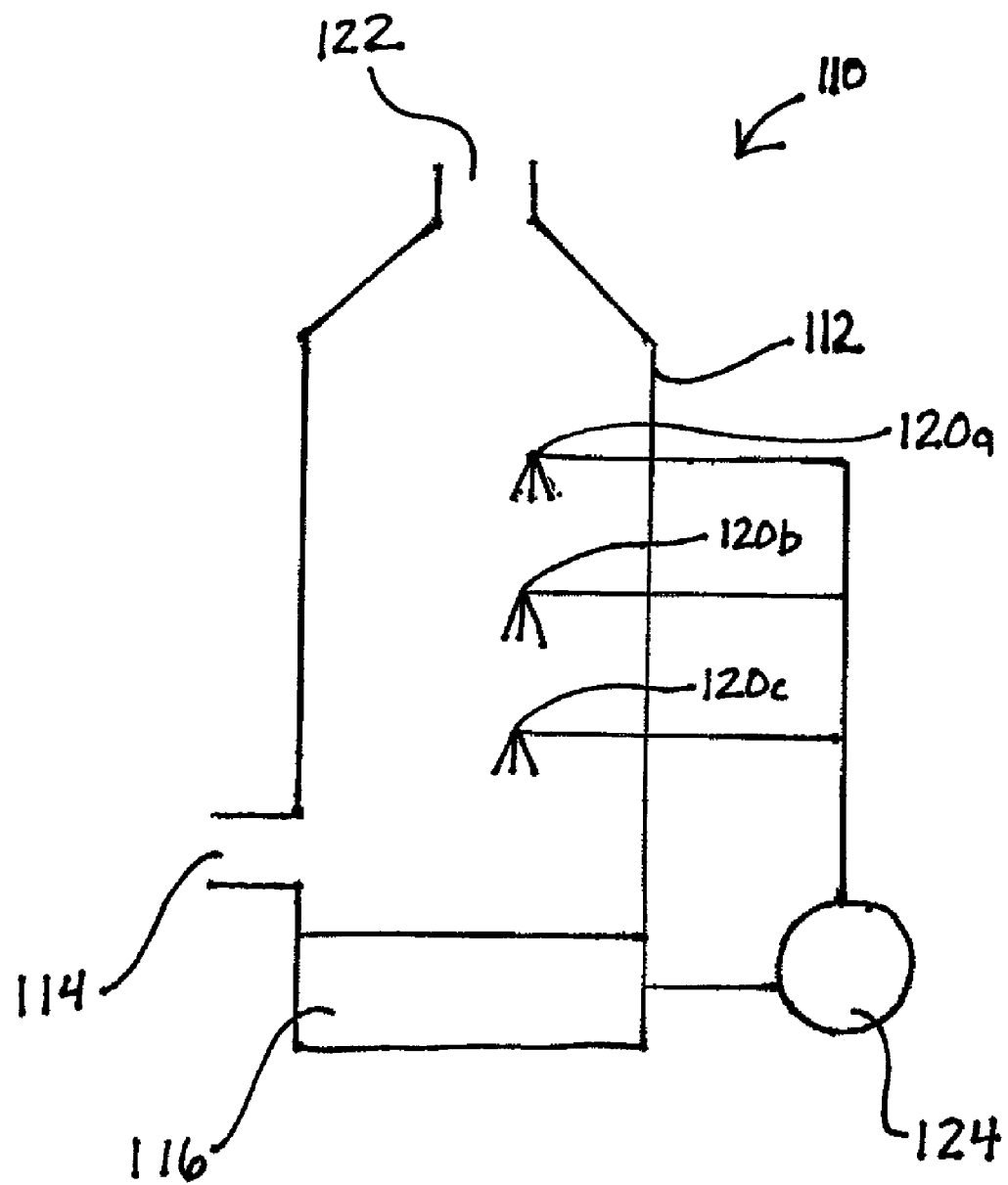
FIG. 2 is a schematic representation of a spray-type air scrubber that can be used in accordance with embodiments of the presently-disclosed subject matter.

Similarly to the packed bed scrubber of FIG. 1, the scrubber 110 of FIG. 2 is comprised of a vertical tank 112 where the influent untreated air enters through a duct 114 located above the sump water 116 located in the bottom of the tank 112.

Above the sump 116 are found nozzle configurations 120a, 120b, 120c where the nozzles provide a water spray that covers the horizontal area of the tank. There can be from about one to about ten such nozzle configurations. The air travels upwards through the water sprays, a de-mister section, and then on out the stack 122.

The water from the sump 116 is pumped up through the nozzle configurations 120a, 120b, 120c and falls back to the sump.

The dicarboxylic acid solution is fed into the sump water 116 or into the suction side of the recirculation pump 124, or into the pressure side of the recirculation pump 124. Normally the solution would be metered in with one of the following: a chemical metering pump, educator, gear pump, progressive cavity pump, or any other pump or device designed to deliver liquid in the required volume. pH control of the sump water is controlled via a pH controller which activates a chemical pump or other device that provides for the addition of an acid or caustic to the sump.

Example 3

Figure 3:
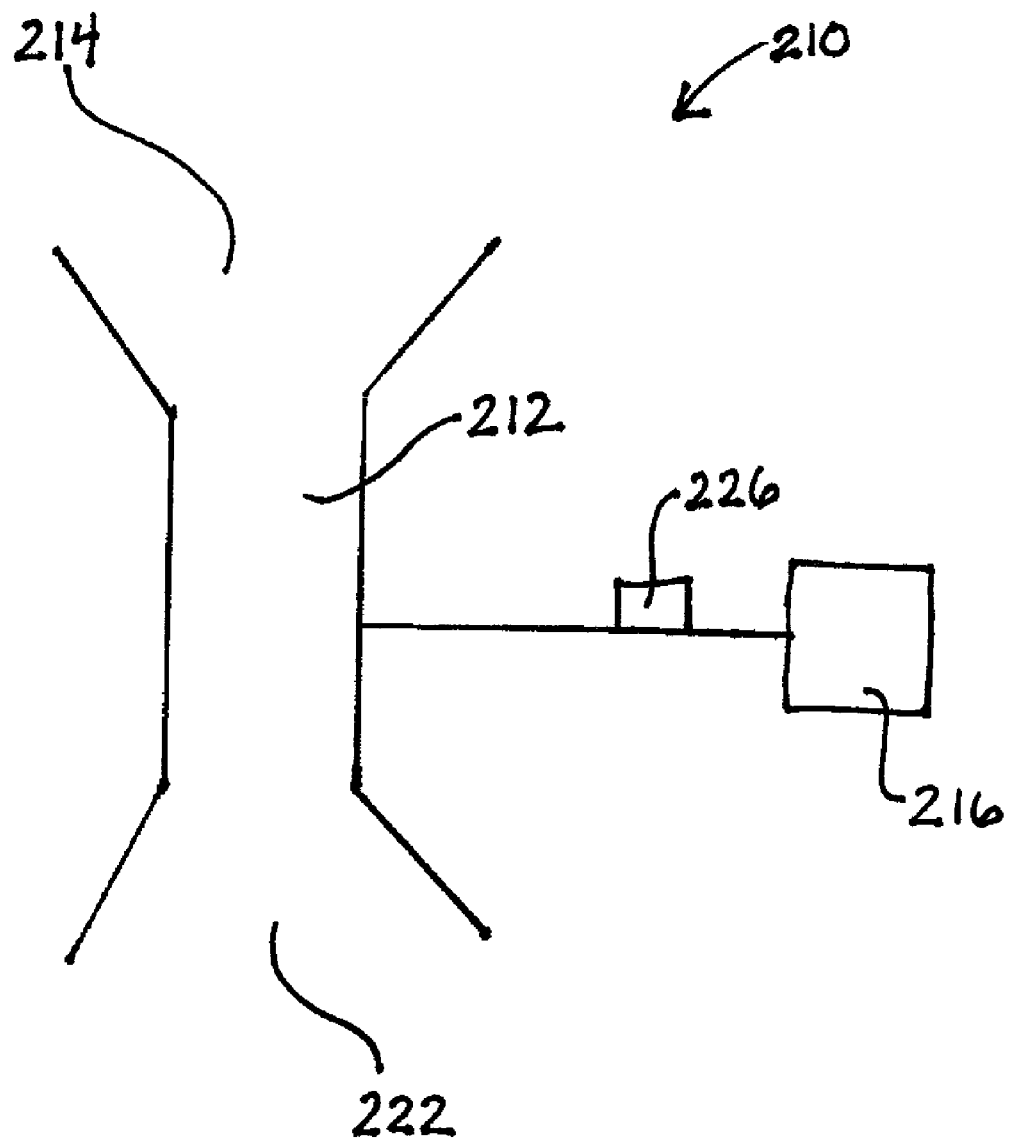
FIG. 3 is a schematic representation of an air scrubber component that can be used in accordance with embodiments of the presently-disclosed subject matter.

FIG. 3 is a simple diagram of an example of a Venturi scrubber 210. Venturi scrubbers can be horizontal or vertical. Venturi scrubbers normally have a sump 216. The water of the sump 216 is sprayed into the throat 212 of the Venturi. The influent untreated air enters the Venturi through a duct 214, and is exposed to the spray of water from the sump 216 as it travels through the Venturi and ultimately exits 222 the Venturi.

The dicarboxylic acid solution is fed into the sump water 216 or into the suction side of the recirculation pump, or into the pressure side of the recirculation pump. Normally the solution would be metered in with one of the following: a chemical metering pump, educator, gear pump, progressive cavity pump, or any other pump or device designed to deliver liquid in the required volume. pH control of the sump water is controlled via a pH controller 226 which activates a chemical pump or other device that provides for the addition of an acid or caustic to the sump.

Example 4

Materials useful for practicing methods described herein can be conveniently included in a kit. An exemplary kit includes at least one of the following components in at least one appropriate container or vial, together with instructions for controlling odor in accordance with the methods described herein. The at least one component can be selected from: a dicarboxylic acid, a scale inhibitor, an oil dispersant, a surfactant, a water-soluble ketone, and a water-soluble aldehyde. When more than one component is provided in the kit, the multiple components can be provided in separate containers or vials, or components can provided together in a container or vial; for example, two or more component can be provided in one container, and two or more different components can be provided in a second container.

As noted, the kit can include instructions. The instructions can describe feeding the one or more components into water circulating in an air scrubber, and monitoring and maintaining the concentration of the one or more components in the circulating water.

The amounts, recommended concentrations and/or ratios of the components can be specifically designed to meet the needs of a particular end user. For example, recommendations in the instructions can depend on the amount and types of contaminants found in the influent or untreated air coming into the air scrubber. The amount and types of contaminants can result in a particular percentage of the one or more components comprising a dicarboxylic acid being provided or recommended. For another example, the level of calcium and magnesium found in the water can affect an amount or percent of a scale inhibitor that is provided or recommended. For another example, the concentration and type of oil and grease found in the influent air stream can affect the type of oil dispersant and the amount/percentage of dispersant that is provided or recommended. For yet another example, the type of aldehyde or ketone provided or recommended can depends on the average temperature of the circulating water, and can be changed to match both temperatures and the concentration level of sulfur-containing contaminants found in the influent air stream. This concentration can also be adjusted for fragrance. For another example, the type of scale inhibitor that is provided or recommended can depend on the level of scale producing compounds. For example at a LSI of less than +1 the scale inhibition can be provided by octylphenylpolyethoxyethanol combined with sodium acrylate. When the LSI scaling index raises above +1 or is between about +1 to about +2.5, the scale inhibitors can be a combination of 1-hydroxyethylidene-1,1-diphosphonic acid and sodium acrylate.

The kit can include pH control materials and/or the instructions can include recommendations regarding pH control and use of pH control materials. Such pH control materials can include any known to those skilled in the art, and can include, for example: sulfuric acid, hydrochloric acid, and/or phosphoric acid. In some cases these pH control materials can be fed into the circulating water separately from the dicarboxylic acid, and other components identified herein, due to chemical incompatibility in their concentrated form.

Appropriate use of the one or more components can be determined, for example, by measuring and/or estimating the contaminants in the air flowing into the air scrubber. Based on the measured and/or estimated total pounds per day to be removed, an amount of each of the one or more components can be metered into the circulating water, which amounts are substantially equal to the stoichiometric amount required, plus any additional amount required to drive the reactions to completion within the required time frame that the air is in contact with the water of the air scrubber. The efficiency of each scrubber varies depending on manufacturer, material of construction, depth of packing, number of nozzles, etc. The efficiency can vary the amount of the one or more components required over stoichiometric level to drive reactions to completion.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

What is claimed is:

1. A method for controlling odor in an air scrubber, comprising:
   providing a dicarboxylic acid;
   contacting the dicarboxylic acid with an odor-causing contaminant through feeding the dicarboxylic acid into water circulating in the air scrubber; and
   maintaining the dicarboxylic acid in a solution at a pH of between about 5.0 to about 8.0.

2. The method of claim 1, wherein the step of maintaining the dicarboxylic acid solution at a pH of between about 5.0 to about 8.0 comprises maintaining the water circulating in the air scrubber at a pH of between about 5.0 to about 8.0.

3. The method of claim 1, further comprising controlling saturation of the water circulating in the air scrubber.

4. The method of claim 1, wherein the odor-causing contaminant is selected from primary amines, secondary amines, tertiary amines, ammonia, mercaptans, thiols, hydrogen sulfide, other sulfide compounds, and combinations thereof.

5. The method of claim 1, wherein the dicarboxylic acid has the formula:

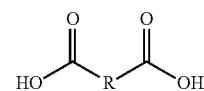

wherein, R is selected from covalent bond, lower alkyl, alkyl, alkenyl, aryl, or any substituted or unsubstituted carbon chain, wherein the resulting dicarboxylic acid is water-soluble.

6. The method of claim 1, wherein the dicarboxylic acid is selected from: oxalic acid, malonic acid, succinic acid, glutaric acid, hexanedioic acid, heptanedioic acid, oxtanedioic acid, nonanedioic acid, decanedioic acid, malic acid, phthalic acid, isophthalic acid, terephthalic acid, and any other water-soluble dicarboxylic acid.

7. The method of claim 1, wherein the dicarboxylic acid is selected from: oxalic acid, malonic acid, succinic acid, glutaric acid, and malic acid.

8. The method of claim 1, wherein the dicarboxylic acid is malic acid.

9. The method of claim 1, and further comprising:
   providing a scale inhibitor, an oil dispersant, a surfactant, a water-soluble ketone, a water-soluble aldehyde, or combinations thereof.

10. The method of claim 1, wherein the dicarboxylic acid is provided at a concentration of at least about 100 part per million.

11. The method of claim 10, wherein the dicarboxylic acid is provided at a concentration of about 100 parts per million to about 2000 parts per million.

12. The method of claim 1, wherein the concentration of dicarboxylic acid is adjusted to a stoichiometric level to match the odor-causing contaminant.

\* \* \* \* \*